US007802541B2

(12) United States Patent
Jones et al.

(10) Patent No.: US 7,802,541 B2
(45) Date of Patent: Sep. 28, 2010

(54) POULTRY VACCINATION APPARATUS AND METHOD

(76) Inventors: Jesse Jones, 4939 Hwy. 278, Emmet, AR (US) 71835; Larry Cox, 240 Hwy. 32 E., Ashdown, AR (US) 71822; Clovis Hicks, 129 Peach Tree Ln, Hope, AR (US) 71801

( * ) Notice: Subject to any disclaimer, the term of this patent is extended or adjusted under 35 U.S.C. 154(b) by 341 days.

(21) Appl. No.: 11/974,583

(22) Filed: Oct. 15, 2007

(65) Prior Publication Data

US 2009/0157038 A1     Jun. 18, 2009

Related U.S. Application Data

(60) Provisional application No. 60/852,228, filed on Oct. 17, 2006.

(51) Int. Cl.
*A01K 37/00* (2006.01)
(52) U.S. Cl. ..................... 119/713
(58) Field of Classification Search ........... 119/713, 119/6.8, 843; 604/156, 131, 144
See application file for complete search history.

(56) References Cited

U.S. PATENT DOCUMENTS

| | | | | |
|---|---|---|---|---|
| 3,570,487 A | * | 3/1971 | Reynolds | 604/20 |
| 3,774,578 A | * | 11/1973 | Randolph et al. | 119/714 |
| 4,375,814 A | * | 3/1983 | Gourlandt | 606/164 |
| 4,446,819 A | * | 5/1984 | Gourlandt | 119/714 |
| 4,681,565 A | * | 7/1987 | Gourlandt | 604/115 |
| 4,758,227 A | | 7/1988 | Lancaster, Jr. et al. | |
| 4,951,610 A | * | 8/1990 | Gourlandt | 606/163 |
| 5,312,353 A | * | 5/1994 | Boggess et al. | 604/144 |
| 5,468,227 A | | 11/1995 | Haskell | |
| 6,565,533 B1 | * | 5/2003 | Smith et al. | 604/144 |
| 6,609,479 B2 | * | 8/2003 | Storer et al. | 119/716 |
| 6,634,319 B1 | | 10/2003 | Zermoglio et al. | |
| 6,789,467 B2 | * | 9/2004 | Johnston et al. | 99/532 |
| 7,232,450 B2 | * | 6/2007 | Gorans et al. | 606/164 |

* cited by examiner

*Primary Examiner*—T. Nguyen
(74) *Attorney, Agent, or Firm*—J. Charles Dougherty

(57) ABSTRACT

An apparatus for providing multiple vaccinations of poultry simultaneously is described. A neck injection, breast injection, two wing injections, and an eye mist or drop may be performed in one operation. The apparatus holds the bird in position for precise location of injections, thereby reducing wasted vaccine. The risk of injury to the bird during the process is minimized by greatly reducing the manual handling of the bird during vaccination. Vaccination costs are also reduced by the reduction of labor otherwise required in this process.

8 Claims, 7 Drawing Sheets

POULTRY VACCINATION APPARATUS AND METHOD

CROSS-REFERENCE TO RELATED APPLICATIONS

The present application claims the benefit of U.S. provisional patent application No. 60/852,228, entitled "Poultry Vaccination Device" and filed on Oct. 17, 2006. Such application is incorporated herein by reference.

STATEMENT REGARDING FEDERALLY SPONSORED RESEARCH OR DEVELOPMENT

Not applicable.

BACKGROUND OF THE INVENTION

The present invention relates to devices and methods for vaccination of poultry, and in particular to such devices and methods capable of providing multiple vaccinations simultaneously in a quick and safe manner.

Modern production methods for poultry (primarily chickens and turkeys, but also including ducks, geese, quail, and other birds raised for protein) involve the housing of birds in a very high-density environment, primarily in order to minimize production costs. As a result of the high-density living arrangements, the birds are susceptible to all sorts of communicable avian diseases. The vaccination of birds under these conditions is an essential part of the production process, preventing disease outbreaks that, in many production houses, could otherwise wipe out many thousands of birds before isolation and containment of the disease could occur. Recent concerns about the spread of avian influenza among humans heighten the risk for producers who fail to properly vaccinate their birds.

The typical method for vaccinating poultry today is a manual process. The inventors believe that this process, as used by typical commercial poultry producers, has remained unchanged for more than fifty years. The birds are first caught by hand, and a vaccine is administered either by a droplet placed in the eye of the bird or an injection into the bird's body or wing, depending upon the type of vaccination. Since numerous vaccinations are generally performed simultaneously in order to save time, the usual process is to have a line of workers, each of whom takes a bird in turn and applies a particular vaccination. The bird is returned to its cage after each worker has applied a vaccination.

Labor is a large cost of poultry production, and since the usual process for poultry vaccination is by its very nature labor intensive, vaccination therefore drives up the costs associated with poultry production. Many poultry producers are experiencing an ongoing labor shortage, which further increases the costs associated with this process. In addition, the necessity of holding the bird still during the vaccination process, and the necessity of passing the bird from worker to worker as each vaccination is applied, results in numerous injuries and even deaths to the birds. The manual process also introduces error into the placement of the vaccination, and thus some vaccinations may not be effective. If the error is caught then vaccine is wasted, otherwise the bird will not be properly vaccinated and risks infection. Finally, manual vaccination places the workers themselves at risk of accidentally injecting themselves with the poultry vaccine. Due to the very high volume of vaccinations performed by workers, this type of accident is not uncommon.

The prior art includes a number of attempts to develop machinery that at least partially automates the process of poultry vaccination. An early attempt was the development of a turntable or wheel whereby a bird was hung by its feet and vaccinated by a circle of workers standing around and below the wheel. After each vaccination, the wheel was spun so that a bird was placed in front of the next worker to provide a vaccination. This process did not reduce the number of laborers required for the vaccination process, and has not seen widespread adoption.

Another and more recent example of an attempt to solve these problems is taught by U.S. Pat. No. 4,758,227 to Lancaster, Jr. et al. This patent teaches a poultry injection system that includes a cradle into which the bird is placed. The bird is held in place manually by the operator holding the bird's legs with one hand and pressing down on the bird with the other hand. A button to activate the machine is positioned where the hand holding the bird's legs can easily reach. The machinery drives two syringes with injection needles that inject vaccine into the bird's breast. This device still requires substantial manual handling of the bird, since the bird is held with both hands during the vaccination. In addition, the device provides no way to administer the eye-drop vaccinations commonly performed on poultry, and thus additional handling of the bird would be required for that step.

U.S. Pat. No. 6,634,319 to Zermoglio et al. teaches a machine for vaccinating chicks, which includes a cavity into which a chick's head is inserted manually for vaccination. When the beak of the chick activates a sensor, arms move to lock the chick's head into place with respect to the machine. A presser stabilizes the chick's neck for insertion of the vaccination needle. When the arms holding the chick in place are withdrawn, the chick falls onto a conveyor belt below. While this device also automates some aspects of the vaccination process, it provides no means for breast or wing insertion of a vaccination needle or eye-drop vaccinations.

U.S. Pat. No. 5,468,227 to Haskell teaches a poultry vaccinator that provides a semi-automatic method of vaccinating a bird by means of a wing injection. The operator must hold the bird in place in the device's trough during operation, while holding the wing out with the hand not holding the bird's feet. Like the other prior art devices discussed herein, this device is not capable of providing all necessary vaccinations, since there is no means of providing breast or eye-drop vaccination, and there is still a substantial manual component of the process since the bird and the bird's wing must be held in place by the operator's hands.

The limitations of the prior art are overcome by the present invention as described below.

BRIEF SUMMARY OF THE INVENTION

The present invention is directed to a poultry vaccination apparatus that is capable of providing multiple poultry vaccinations simultaneously while securely holding the bird in place to minimize the risk of injury or death to the bird during the process. In a preferred embodiment, the apparatus provides a neck injection, two wing injections, and an eye mist or drop in one simple, automated operation. The apparatus moves the bird into position for precise location of injections, thereby reducing wasted vaccine. The risk of injury to the bird during the process is minimized by greatly reducing the manual handling of the bird during vaccination. Vaccination costs are also reduced by the reduction of labor otherwise required in this process. The possibility of a worker injuring him or herself by accidental vaccination is greatly reduced.

It is therefore an object of the present invention to provide for an improved method of providing multiple types of poultry vaccinations simultaneously.

It is a further object of the present invention to provide for a method of reducing the manual labor involved in the poultry vaccination process.

It is also an object of the present invention to provide for a method of vaccinating poultry that reduces the quantity of vaccine wasted during the vaccination process.

It is also an object of the present invention to provide for a method of vaccinating poultry that reduces the likelihood of injury or death for the vaccinated bird.

It is also an object of the present invention to provide for a method of vaccinating poultry that holds a bird more securely in a precisely desired position during vaccination.

It is also an object of the present invention to provide for a method of vaccinating poultry that greatly reduces the likelihood of a worker injury due to accidental self-injection.

These and other features, objects and advantages of the present invention will become better understood from a consideration of the following detailed description of the preferred embodiments and appended claims in conjunction with the drawings as described following.

DETAILED DESCRIPTION OF THE PREFERRED EMBODIMENT(S)

Figure 1:
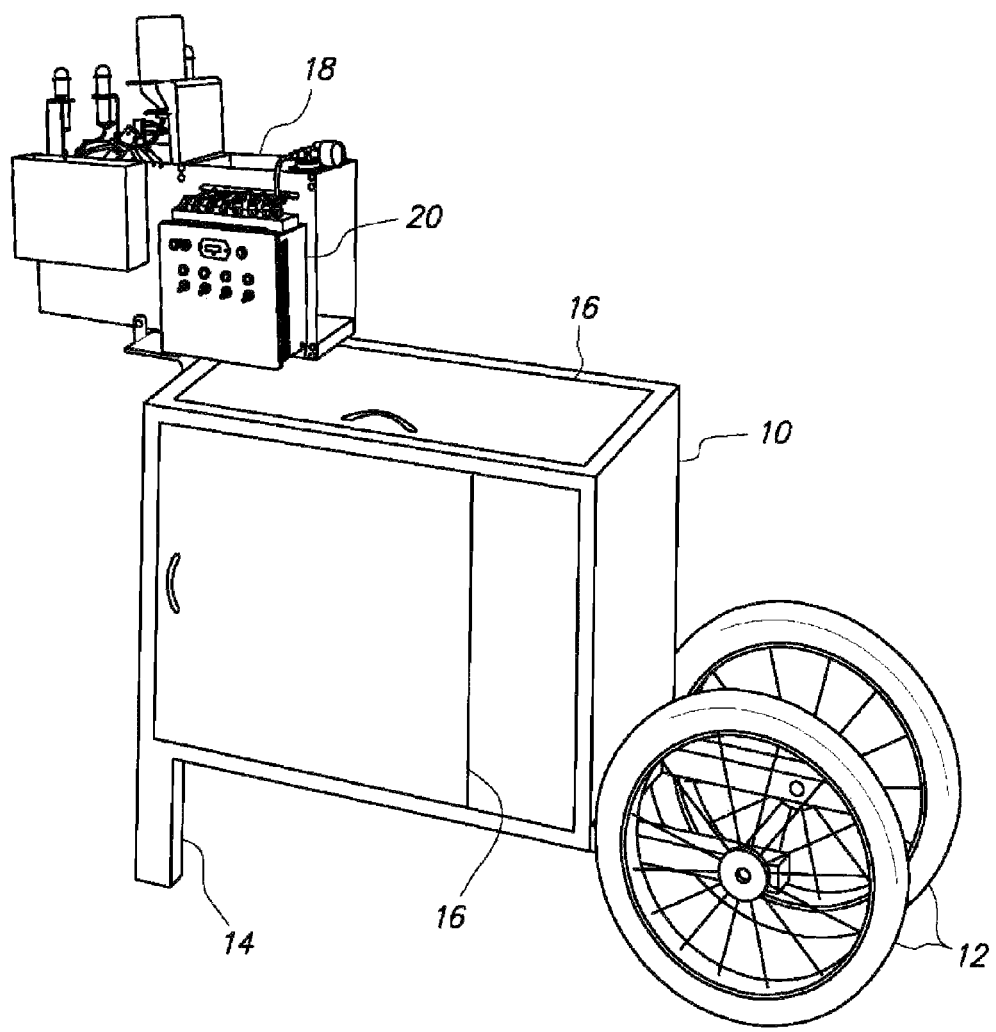
FIG. 1 is a perspective view of a preferred embodiment of the present invention.

With reference to FIG. 1, the major components of a preferred embodiment of the present invention may be described. Cart 10 provides a frame for the preferred embodiment in order that all of the various components may be easily and safely transported to and from the location where vaccinations will occur, typically a poultry production facility. Wheels 12 and feet 14 provide support for cart 10. The device may be easily moved by picking up the front end of the device such that feet 14 are lifted from the ground, at which time wheels 12 may be used to move cart 10 about in a fashion similar to a wheelbarrow. Doors 16 on cart 10 provide access to storage areas for equipment that may be used during vaccination, such as gloves and gowns for the operator. Vaccination chamber frame 18 mounts at the top front of cart 10, preferably at a level where an average-height adult may easy insert a bird for vaccination without stooping, as will be described in more detail below. Frame 18 provides a support structure for the various components of the vaccination chamber. Control panel 20 mounts at the right side of vaccination chamber 18, providing simple and easy access to the operator to the various controls necessary for operating the device.

Figure 5:
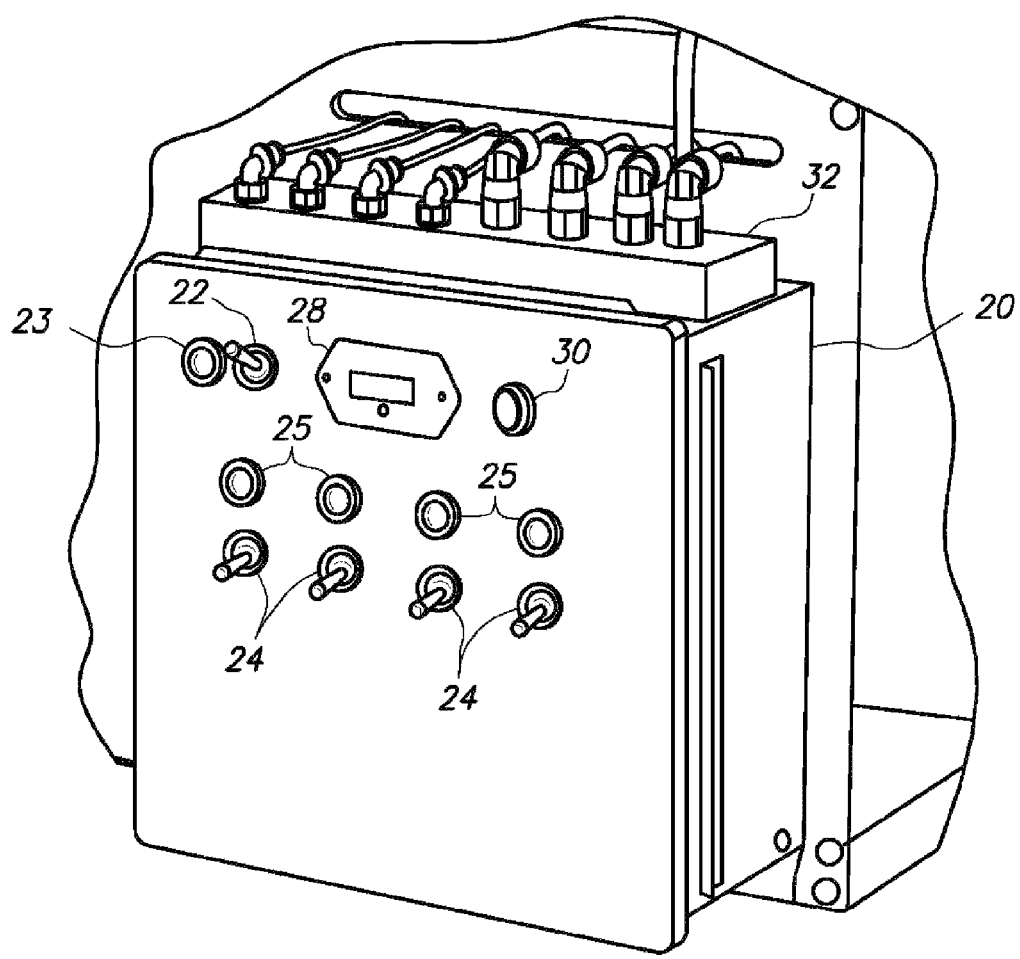
FIG. 5 is a detail view of a control panel according to a preferred embodiment of the present invention.

Referring now to FIG. 5, control panel 20 may be described in greater detail. Master toggle switch 22 provides a master on/off power function for the device. Master indicator 23 is preferably an LED light that activates to show that the device is powered on. Toggle switches 24 provide power to each of the individual vaccinations, in this example being two wing inoculations, a neck inoculation, and an eye drop or mist. Indicators 25 are LED lights that activate to show that each of these vaccination routines is ready for operation. Each of these indicators described herein may preferably be a green LED light, but in other embodiments may be any other sort of indicator to show a ready condition as are known in the art. Likewise, each of the switches described herein are preferably simple mechanical toggle switches of a kind well known in the art, but could alternatively be any other type of switch capable of switching power on and off with respect to a particular electrical circuit. Counter 28, which in the preferred embodiment functions similar to an analog odometer typically found in older automobiles, provides an on-going count of the number of vaccinations that have been performed using the device. The count on counter 28 may be reset by depressing reset button 30. Manifold 32 provides pneumatic and electrical connections to the various controls of control panel 20 as are known in the art in order to power and control the various functions of the device, as described in greater detail below. A battery of conventional sort (not shown) may be disposed within cart 10 to provide system power to the device.

Figure 2:
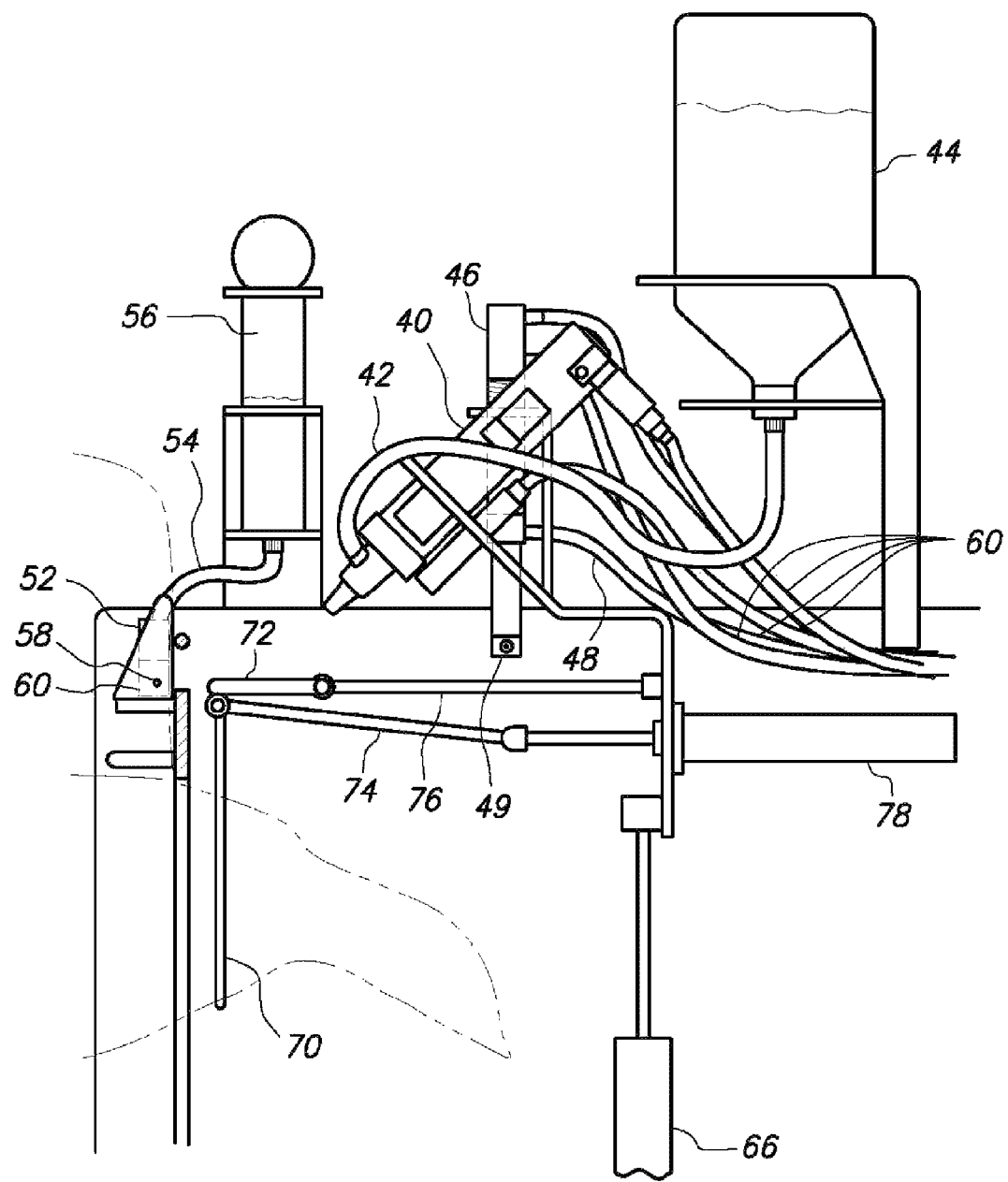
FIG. 2 is a partial cut-away, side elevational view of a vaccination chamber section of a preferred embodiment of the present invention when the device is ready to receive a bird for vaccination.
Figure 3:
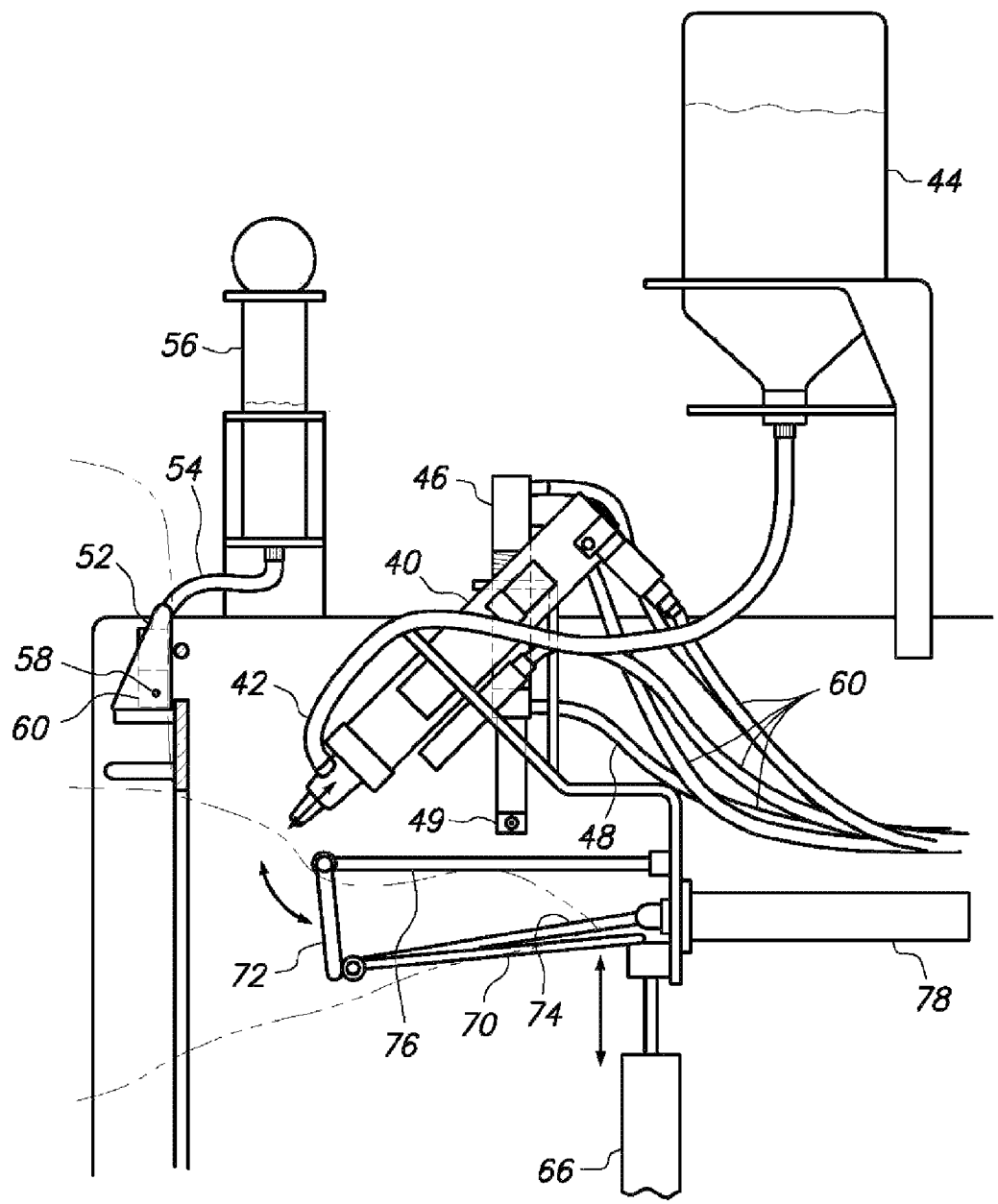
FIG. 3 is a partial cut-away, side elevational view of a vaccination chamber section of a preferred embodiment of the present invention during vaccination of a bird.
Figure 4:
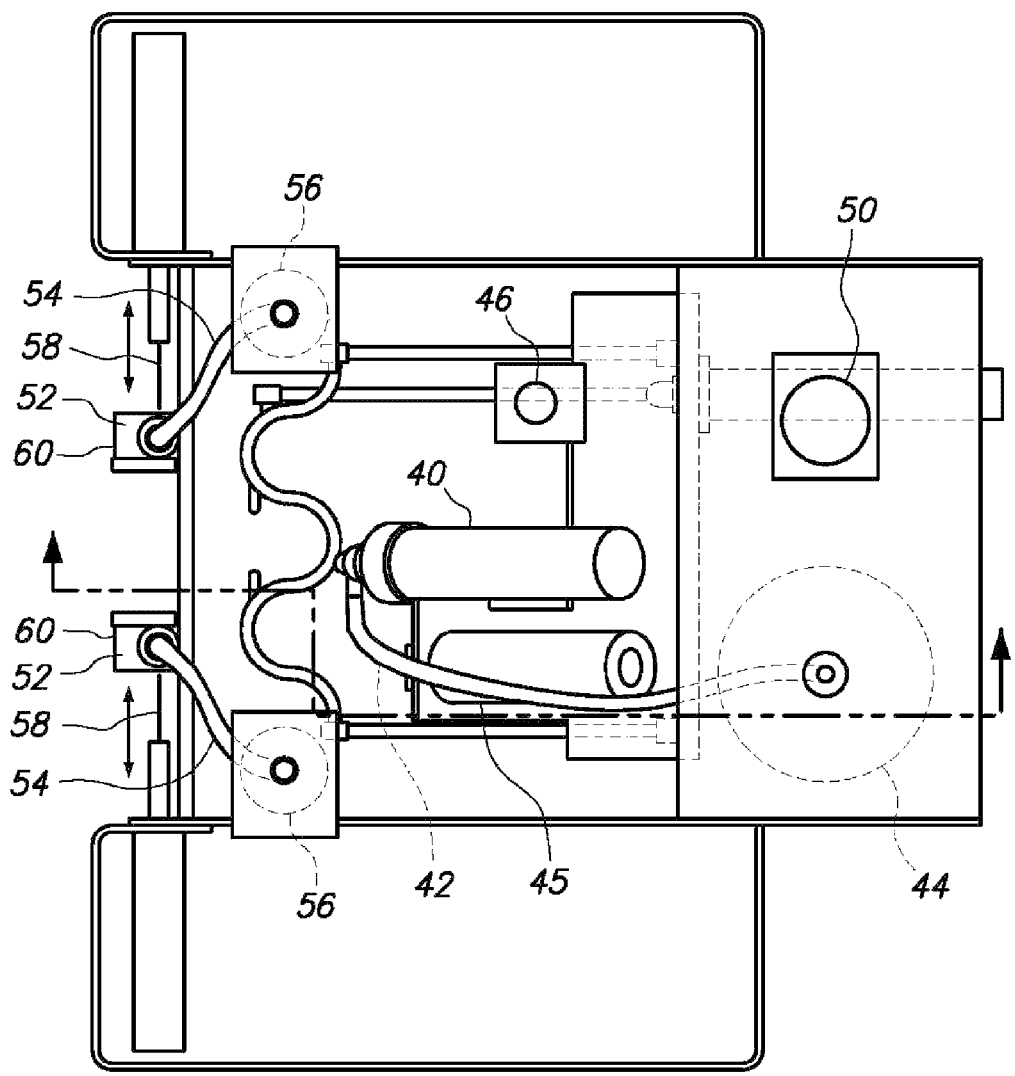
FIG. 4 is a top plan view of a vaccination chamber section of a preferred embodiment of the present invention, showing by dotted line the sectional view of FIGS. 2 and 3.

Referring now to FIGS. 2-4, the major components of the vaccination chamber of a preferred embodiment of the present invention may be described. Neck injection unit 40 is positioned at an angle with respect to the vaccination chamber, such that, as will be described below, it aligns with the nape of the neck of a bird during the vaccination process. Maerck's disease vaccine is a common disease vaccine administered by this method. Vaccine is fed to neck injection unit 40 by gravity through neck injection vaccine tube 42 from neck vaccine bottle 44. The operation of neck injection unit 40 is powered by neck unit pneumatic cylinder 45.

Eye injection unit 46 is positioned vertically with respect to the vaccination chamber, such that, as will be described below, it aligns with the eye of a bird when the bird is properly positioned in the device during the vaccination process. Eye injection unit 46 may either be a spray- or drop-type injection unit, both of which are commonly used in the art as a means of dispensing certain types of vaccines to birds by means of the eye. In the illustrated preferred embodiment, a spray-type injection means is used, incorporating spray nozzle 49. Newcastle and bronchitis vaccines are common disease vaccines administered by this method. Vaccine is fed to eye injection unit 46 by gravity through eye injection vaccine tube 48 from eye vaccine bottle 50.

The two wing injection units 52 are positioned horizontally with respect to the vaccination chamber, pointing inwards towards each other, such that, as will be described below, they align with the underside of the web portion of each wing of a bird when the bird is properly positioned in the device during the vaccination process. Fowl pox is a common disease vaccine administered by this method. Vaccine is fed to each of the two wing injection units 52 by gravity through wing injection tubes 54 from wing vaccine bottles 56. It will be seen that vaccine is delivered to wing injection needles 58 by passing needles 58 through vaccine reservoir 60 of wing injection units 52, rather than having vaccine delivered through a hollow needle as is customary for vaccine injection methods. This method of vaccine delivery helps insure that only uncontaminated vaccine is delivered to the wing web of the vaccinated birds.

The operation of each of neck injection unit 40, eye injection unit 46, and wing injection units 52 are powered by pneumatic cylinders, including wing injection unit pneumatic cylinder 45. Other pneumatic cylinders 64, 66, and 78 power the apparatus for catching and holding a bird in place. Compressed air is delivered to these units by means of air lines 60 (some of which are omitted in the drawings for clarity). The powering of pneumatic cylinders using a compressed air source for various purposes is well known in the art. A compressed air tank (not shown) may be positioned within cart 10 for purposes of powering air lines 62. Alternatively, an electrically powered air compressor (not shown) may be positioned on-board within cart 10 in order to provide compressed air either to the compressed air tank within cart 10 or directly to air lines 62. In the case where compressed air is provided directly by an air compressor, electrical power must be available at all times during operation of the device, and the preferred embodiment therefore include a compressed air tank to store compressed air to power the device. It may be seen that in alternative embodiments other forms of power other than pneumatic power may be used, such as, for example, all-electrical components or hydraulic components.

Figure 2A:
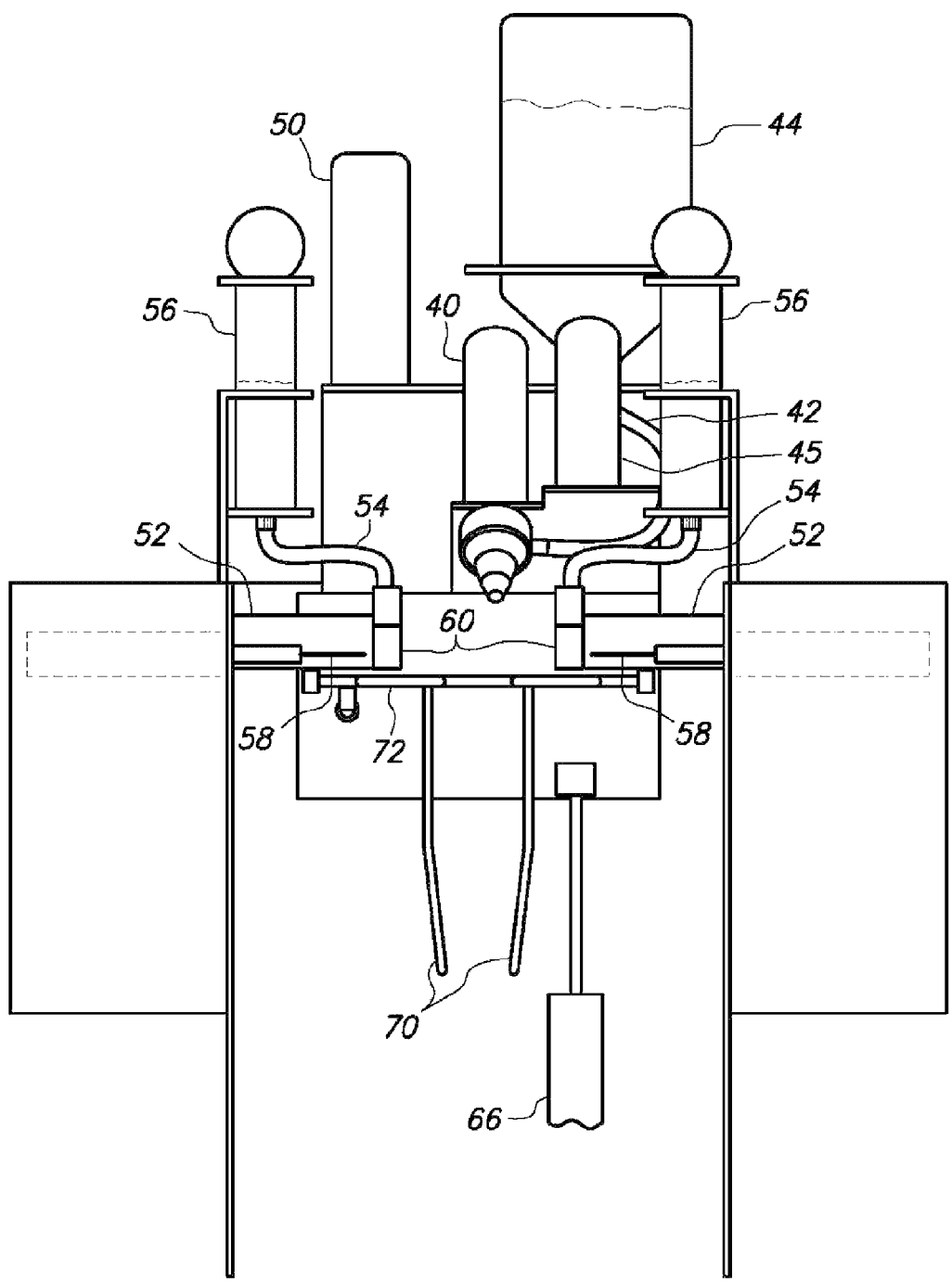
FIG. 2A is a partial cut-away, front elevational view of a vaccination chamber section of a preferred embodiment of the present invention when the device is ready to receive a bird for vaccination.

Referring again to FIGS. 2-4, those elements of the device used to hold a bird in place during vaccination may now be described. Forks 70 begin pointed in a downwardly direction, such that the head of the bird may be received therebetween, as shown in FIGS. 2, 2A, and 4. S-bar 72 is linked at the top of forks 70, and lies in a horizontal position before vaccination takes place. S-bar 72 is held in place pivotally with respect to the vaccination chamber by S-bar support 76. Manipulation of S-Bar 72 and forks 70 is accomplished by means of linkage 74, connected to linkage pneumatic cylinder 78.

The operation of the device for bird vaccination may now be described with reference to FIGS. 2-5. Power to the device is turned to the "on" setting by means of master toggle switch 22, and the appropriate toggle switches 24 may be set in order to activate various inoculations that may be administered by the device. Preferably, all four toggle switches 24 of the preferred embodiment are switched to the "on" position, such that an eye mist/drop, neck injection, and two wing injections will be administered simultaneously upon each activation. The actual activation of the device once a bird is inserted may preferably be performed by means of a wired or wireless remote control (not shown), which may preferably be stored within cart 10 when not in use. The remote control may be hand- or foot-operated. Such remote control devices as may be employed with the invention for this purpose are known in the art.

When a bird is inserted into the machine as shown in FIG. 2, the bird should be positioned by the operator such that its wings are held together, outstretched above the bird. Preferably, the bird is held by the wings such that the body and head drape below the wings. The head of the bird is then inserted between forks 70 when forks 70 are in the downwardly pointed position as shown in FIGS. 2, 2A, and 4. The underside of the web portion of the wings of the bird will be aligned with and between needles 58 of wing vaccination units 52.

Figure 3A:
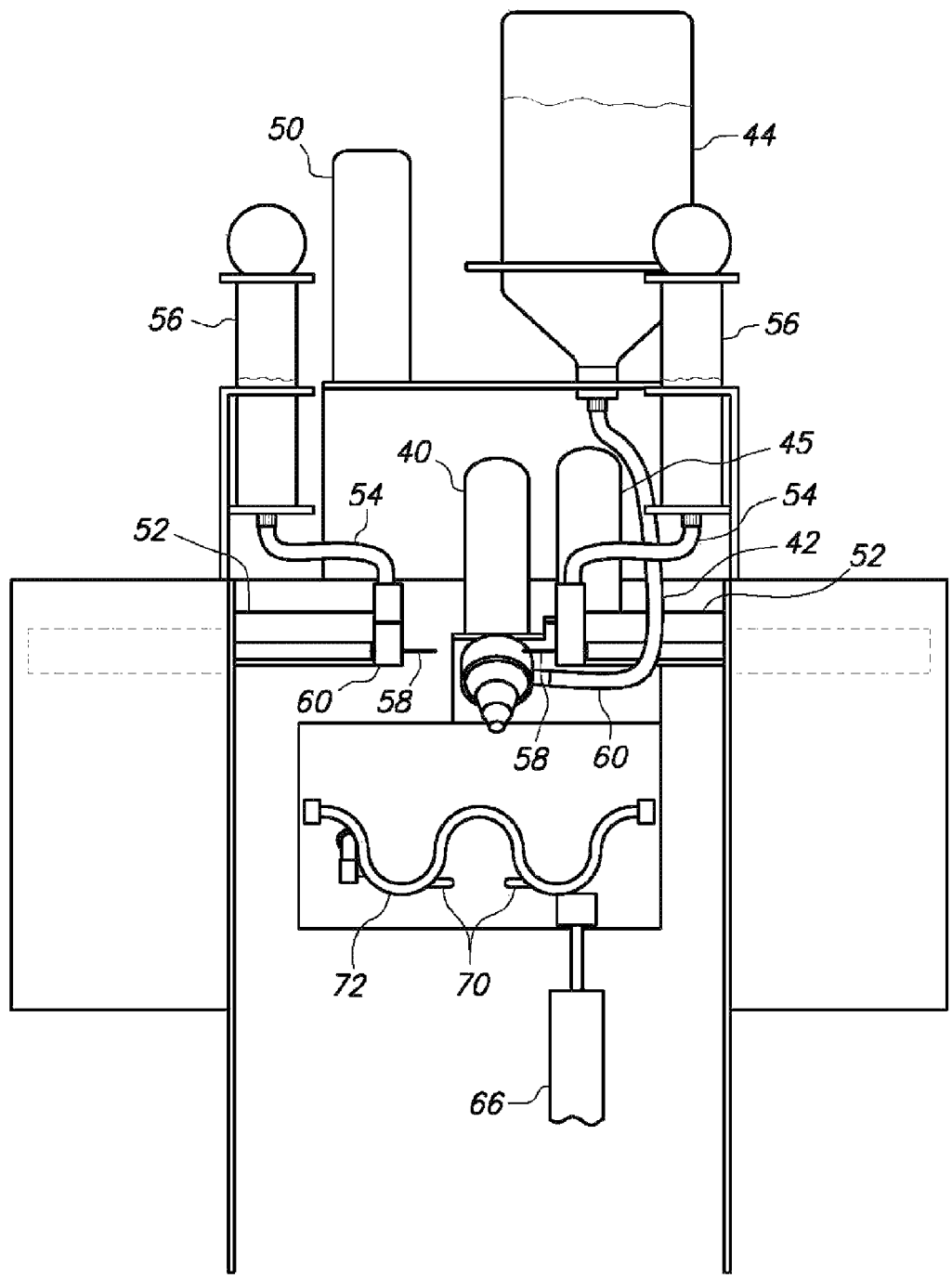
FIG. 3A is a partial cut-away, front elevational view of a vaccination chamber section of a preferred embodiment of the present invention during vaccination of a bird.

Once the bird is in position, the machine may be activated, preferably by means of depressing a single button on the remote control. When this occurs, a series of actions take place that result in vaccination of the bird. First, linkage cylinder 78 retracts, causing linkage 74 to pull rearwardly on S-bar 72, swinging forks 70 in a back and upward configuration as shown in FIGS. 3 and 3A. The position of S-bar 72 on the back of the bird's neck, along with the action of forks 70 drawing the bird's neck inward into the vaccination chamber, results in a proper positioning of the bird to receive the appropriate vaccinations. It may be noted that the upwardly curved portion of S-bar 72 rests on the back of the bird's neck. Next, cylinder 45 activates to extend neck vaccination unit 40 downwardly into position to vaccinate the bird. Finally, spray nozzle 49 of eye vaccination unit 46, two wing vaccination units 52, and neck vaccination unit 40 are all activated in order to inject vaccine into the eye, each wing web area, and neck of the bird, respectively, in a simultaneous fashion. Once the process is completed, S-bar 72 and forks 70 return to the initial position shown in FIGS. 2, 2A, and 4, and the bird may be safely removed from the device with vaccination completed. The entire operation may be performed in a matter of a few seconds using the preferred embodiment of the present invention.

The present invention has been described with reference to certain preferred and alternative embodiments that are intended to be exemplary only and not limiting to the full scope of the present invention as set forth in the appended claims.

What is claimed is:

1. A bird vaccination apparatus, comprising
   (a) at least one vaccination unit operable to vaccinate a bird;
   (b) a receiving unit, operable to receive a bird and further operable to move a bird into position to receive a vaccination from said vaccination unit, wherein said receiving unit comprises a pair of forks, wherein said forks are adapted to receive a neck of the bird therebetween;
   (c) a bar pivotally connected to said forks, wherein said bar is adapted to receive a top of the neck of the bird; and
   (d) a linkage connected to said forks and said bar, wherein said linkage adapted to pivot said bar downwardly toward the ground and pivot said forks such that the beak of the bird is supported by said forks, whereby the bird whose neck is held in place by said bar and said forks is brought forward and into position for receiving a vaccination in said bird vaccination apparatus.

2. The apparatus of claim 1, wherein said vaccination unit comprises a neck vaccination unit operable to inject a vaccine into the neck of the bird.

3. The apparatus of claim 2, wherein said vaccination unit further comprises an eye vaccination unit, wherein said eye vaccination unit comprises at least one of an eye mist vaccination unit comprising a spray nozzle and an eye droplet vaccination unit.

4. The apparatus of claim 3, wherein said vaccination unit further comprises at least one wing vaccination unit.

5. The apparatus of claim 4, wherein said wing vaccination unit is positioned horizontally with respect to said bird vaccination apparatus, and directed inwardly so as to be operable to vaccinate an underside of a web portion of a wing of the bird.

6. The apparatus of claim 5, wherein said wing vaccination unit comprises a vaccine reservoir comprising a horizontal passageway, and a needle disposed to pass through said horizontal passageway of said vaccine reservoir before entering the web portion of the wing of the bird.

7. The apparatus of claim 5, wherein said wing vaccination unit comprises two wing vaccination units, each disposed in an opposed position to vaccinate the underside of the web portion of each of two wings of the bird.

8. An apparatus for injecting vaccines into a bird, comprising:
   (a) a vaccine chamber;
   (b) a bar pivotally connected to said vaccine chamber;
   (c) a pair of forks connected to said bar;
   (d) a linkage connected to said forks and said bar;
   (e) a first activation means in communication with said linkage and said vaccine chamber;
   (f) a neck vaccination unit connected to said vaccine chamber;
   (g) a second activation means in communication with said neck vaccination unit;
   (h) a wing vaccination unit connected to said vaccine chamber;
   (i) a third activation means in communication with said wing vaccination unit;
   (j) an eye vaccination unit connected to said vaccine chamber; and
   (k) a fourth activation means in communication with said eye vaccination unit.

* * * * *